United States Patent [19]

MacRae et al.

[11] 4,344,930
[45] Aug. 17, 1982

[54] SKIN CARE SPONGE

[75] Inventors: David M. MacRae, Beecroft, Australia; Karl H. Roberts, Flemington, N.J.

[73] Assignee: Colgate-Palmolive Company, New York, N.Y.

[21] Appl. No.: 187,374

[22] Filed: Sep. 15, 1980

Related U.S. Application Data

[63] Continuation of Ser. No. 627,421, Oct. 30, 1975, abandoned.

[51] Int. Cl.³ .................... A61K 9/70; A61L 15/00
[52] U.S. Cl. .................................. 424/28; 424/59; 424/60; 424/63; 424/65; 424/73; 424/80; 424/81; 424/184; 424/150; 424/341; 424/347; 424/357; 424/358; 424/361; 424/362; 424/365; 424/366
[58] Field of Search ............ 424/28; 260/332, 2.5 AG

[56] References Cited

U.S. PATENT DOCUMENTS

| | | | |
|---|---|---|---|
| 140,126 | 6/1873 | Field | 424/62 |
| 2,999,823 | 9/1961 | Dombrow | 260/2.5 AG |
| 3,002,937 | 10/1961 | Parker et al. | 260/2.5 |
| 3,007,883 | 11/1961 | Schmidt et al. | 260/2.5 |
| 3,087,900 | 4/1963 | Brown | 260/2.5 AG |
| 3,262,450 | 7/1966 | Elias | 424/28 X |
| 3,708,435 | 1/1973 | Starkman | 424/78 |
| 3,746,683 | 7/1973 | Salyer et al. | 260/332 X |
| 3,810,841 | 5/1974 | Richter | 252/91 |
| 3,821,130 | 6/1974 | Barron et al. | 260/2.5 AG |
| 3,896,807 | 7/1975 | Buchalter | 424/28 |
| 4,002,173 | 1/1977 | Manning et al. | 424/28 X |
| 4,024,871 | 5/1977 | Stephenson | 424/28 X |
| 4,189,467 | 2/1980 | von Bittera et al. | 424/28 X |

Primary Examiner—Dale R. Ore
Attorney, Agent, or Firm—Herbert S. Sylvester; Murray M. Grill; Norman Blumenkopf

[57] ABSTRACT

A hydrophilic open-celled poly (urea/urethane) sponge derived from a prepolymer produced by the reaction of a polyoxyalkylene polyol with a stoichiometric excess of an organic polyisocyanate, said sponge containing substantially uniformly distributed throughout the pores thereof a readily releasable skin care composition and methods of making same and using same for treating skin.

It has of course long been known to treat the skin for various purposes by applying thereto a skin care composition, such application being commonly effected by first impregnating an absorbent fibrous pad or sponge applicator with the composition, or supplying a quantity of such composition to the surface of the pad or sponge applicator, and then transferring said composition to the skin by wiping and rubbing same with the applicator. This method is subject to certain disadvantages, among which are the tiresome and time-consuming repetitive step of first supplying the applicator with a quantity of the composition, the difficulty of controlling the amount of composition so applied to the skin, the tendency to permanently or temporarily misplace the container holding the composition, and the like.

10 Claims, No Drawings

SKIN CARE SPONGE

This is a continuation of application Ser. No. 627,421, filed Oct. 30, 1975, now abandoned.

U.S. Pat. No. 3,002,937 discloses a polyester-urethane sponge having specified proportions of large and small cells and containing a releasable detergent but no skin care component as such, and the method of producing same is further disadvantageous in requiring careful selection of the emulsifying agent employed in the foaming reaction and the use of small proportions of the bubble or cell producing water reactant, thereby limiting the amount of detergent dissolved therein for incorporation in the foaming reaction and resulting impregnated sponge.

U.S. Pat. No. 3,810,841 also discloses a polyesterurethane sponge containing a releasable synthetic detergent composition, the method of producing same also involving the use of relatively small proportions of water reactant and incorporating the detergent, optionally in combinations with a dry emollient such as ethoxylated lanolin or high molecular weight polyethylene glycols, in the form of dry solid particles in the non-aqueous polyurethane-forming reactant prior to addition thereto of the water reactant. This method is thus further disadvantageous in requiring careful control of the sizes of the dry solid particles to conform with the cell strand thicknesses and the cell or pore sizes of the sponge, in being limited to the use of dry solid particles as releasable functional agents, and their addition only to the non-aqueous polyurethane-forming reactant and none to the water reactant, thereby sacrificing the homogenizing and/or solubilizing action of water.

U.S. Pat. No. 3,007,883 discloses a polyurethane sponge also prepared with a small proportion of water reactant, the foaming reaction being conducted in the presence of a small proportion of lecithin, optionally with an emulsifier to control the pore structure of the sponge. The patent refers to the prior use of surface active agents, including lanolin and lecithin, as emulsifying agents to control pore size, but neither such prior art nor the patented subject matter involves, teaches or contemplates a sponge product impregnated with a releasable functional agent, much less a skin care composition.

Further, most if not all of the foaming procedures of the above-discussed patents involve unduly long setting or curing periods.

It is an object of this invention to provide a device and methods which will not be subject to one or more of the above disadvantages. Another object of the invention is the provision of an improved form of skin care sponge. Still another object of the invention is the provision of a sponge product containing relatively large amounts of skin care composition in readily releasable form and over longer periods of time or cycles of use. A further object of the invention is the provision of improved methods for producing such products. Yet a further object of the invention is the provision of such methods involving shorter setting or curing periods and/or better means of controlling the foaming reaction and the structure of the resulting sponge and the like. And a still further object of the invention is the provision of improved methods of treating skin employing such products. Other objects and advantages will appear as the description proceeds.

The attainment of the above objects is made possible by this invention which includes the provision of a hydrophilic open-celled poly (urea/urethane) sponge derived from a prepolymer produced by the reaction of a polyoxyalkylene polyol with a stoichiometric excess of an organic polysocyanate, said sponge containing substantially uniformly distributed throughout the pores thereof a readily releasable skin care composition and methods of making same and using same for treating skin.

According to a further aspect of this invention, the above-defined sponge is prepared by reacting said prepolymer with an aqueous dispersion (including emulsion or solution) of the skin care composition containing about 30 to 200% of water by weight of the prepolymer. The water in said dispersion reacts in known manner with isocyanate groups in the prepolymer to release carbon dioxide gas bubbles which produce the desired foam or sponge product containing the in situ impregnated skin care composition substantially uniformly distributed throughout its pores in readily releasable form due to the open or reticulated pore or cell structure of the product.

According to a still further aspect of this invention, an improved skin treating method is provided simply by rubbing or wiping the skin with the above-defined impregnated sponge, desirably after first moistening the sponge with water or other aqueous medium to facilitate release of the skin care composition therefrom and, when a flexible sponge is employed, to soften the sponge. The sponge can be used repeatedly, additional amounts of skin care composition being released each time by suitable squeezing of the sponge. When the skin care composition is a liquid, e.g., an oil, the physical squeezing action is sufficient to release the composition to the surface of the sponge, but desirably such release is facilitated by the emulsifying action of surface active agents in the composition. When the skin care composition is a fatty, unctuous, greasy, or slippery solid, the physical squeezing action is generally insufficient and release to the surface of the sponge must generally be aided or made possible by the emulsifying action of said surface active agent in the composition, in conjunction with the sponge-moistening aqueous medium. When such surface active agent is present in the skin care composition, it will accordingly be understood that most if not all the emollient will be applied to the skin in the form of an oil-in-water or water-in-oil emulsion, or an aqueous dispersion.

When the sponge is finally depleted of its supply of skin care composition, it may be employed in the manner of an unimpregnated natural or synthetic sponge. The sponge products per se generally have densities of about 3 to 6 lbs./ft.$^3$, have a wide range of pore sizes varying from about 30 to 100 pores per inch (ppi), and hold about 10 to 20 times their own weight of water.

Methods of preparing hydrophilic open celled poly (urea/urethane) sponges or foams from an isocyanate capped prepolymer produced by reaction of a polyoxyalkylene polyol with a stoichiometric excess of an organic diisocyanate, by addition thereto and reaction therewith of suitable proportions of water, especially relatively large amounts of water ranging from about 30 to 200% by weight of the prepolymer, are known and no claim is accordingly made thereto per se. For example, reference is made to such methods and products disclosed in U.S. Pat. No. 3,833,386, which disclosures are incorporated herein by such reference. Somewhat similar disclosures are to be found in U.S. Pat. Nos. 3,598,772 and 3,171,820, in "German Plastics Practice" published by Debell and Richardson, 1946, Chapter 21, "Plastic Foam," pages 462–465 and in "Papers Presented at the Atlantic Meeting: Synthesis of Isocyanate Polymers" published by the American Chemical Society, Division of Paints, Plastics and Printing Ink Chemistry, September, 1956. Applicants however claim as their essential inventive concept the inclusion or dispersion of an emollient composition, especially those of the type disclosed below, into the said water reactant prior to its admixture and reaction with said prepolymer, thereby enabling the attainment of the desired improved and unexpected results.

According to a preferred embodiment, the isocyanate capped prepolymer is formulated in such a manner as to give crosslinked, three dimensional network polymers on reaction with water to cause foaming, namely by use of a prepolymer having an average isocyanate functionality greater than 2 and up to about 6 or more depending on the composition of the polyol and capping agent components. In generaly, such prepolymers may be prepared by reacting a polyol having an average hydroxyl functionality greater than 2, such as polyoxyethylenated glycerol, trimethylolpropane, trimethylolethane, tetramethylolbutane, pentaerythritol, or sucrose or mixtures thereof or the like, with a stoichiometric excess of an organic, preferably aromatic, diisocyanate or polyisocyanate or mixture thereof.

Alternatively, any polyoxythylenated polyol or mixture thereof may be reacted with a polyisocyanate having an average isocyanate functionality greater than 2 such as triphenyl methane-4,4',4"-triisocyanate, benzene-1,3,5-triisocyanate, toluene-2,4,6-triisocyanate, PAPI (Upjohn; polymethylene polyphenylisocyanate having nearly 3 isocyanate groups per molecule and an isocyanate equivalent weight of 133; U.S. Pat. No. 2,683,730), or mixtures thereof or the like.

The polyoxyethylene polyol reactants are water soluble reaction products derived from the polymerization of ethylene oxide in the presence of a polyhydroxy compound such as water, ethylene glycol, propylene glycol, butylene glycol, diethylene glycol, and the polyhydroxy compounds described above and may have a weight average molecular weight of about 200 to 20,000, preferably about 600 to 6,000. These polyols may contain up to 40 mole percent, preferably up to 25 mole percent or less of a relatively hydrophobic comonomer such as propylene or butylene oxide in the form of a random or block copolymer.

Useful polyisocyanates other than those referred to above include the following diisocyanates: xylene-, chlorophenylene-, diphenylmethane-4,4'-, naphthalene-1,5-, 3,3'-dimethyl-4,4'-biphenylene-, 2,2',5,5'-tetramethyl-4,4'-biphenylene-, 4,4'-sulfonylbis (phenyl)-, 4,4'-methylene orthotolyl-, hexamethylene-, ethylene-, trimethylene-, tolyene-diisocyanate, the corresponding isothiocyanates, and the like. The mixed 80/20 tolylene 2,4/2,6 isomers are preferred.

A stoichiometric excess of the polyisocyanate reactant is generally employed to assure complete capping, such as in about a 1.1 to 4:1 preferably about 2 to 3:1 molar ratio of isocyanate to hydroxyl. The reaction may be carried out in an inert moisture-free atmosphere such as under a nitrogen blanket at atmospheric pressure at a temperature in the range of from about 0° C. to about 120° C. for up to 20 or more hours.

In contrast to the usual polyurethane foam reactions involving use of the theoretical ½ mole of water per mole of —NCO, the presently preferred process employs from about 30 to 200% of water by weight of the capped prepolymer, or about 6.5 up to about 390 moles of water, desirably about 20 to 200 moles of water per NCO group. This large amount of water aids in enabling the attainment of improved and unexpected results by inclusion therein of increased amounts of the skin care composition in addition to improvements in the properties of the sponge structure per se.

The skin care compositions useful in the practice of this invention are well known per se and may have a wide variety of uses, functions or purposes. As exemplary of such uses and compositions, in the physical form of liquids, oils, creams, lotions, pastes, ointments, and (preferably fatty, unctuous, greasy, waxy or slippery), solids and the like, there may be mentioned baby skin preparations, bath oils, skin softening, conditioning, rejuvenating, relaxing, soothing, analgesic, antiseptic, antibiotic, germicidal, cleansing, after-shave, sunscreen, emollient, make-up, protective, perfume, deodorant, anti-perspirant, burn, massage, liniment and other skin preparations and the like. In addition to the necessary dosage amount of any active functional ingredient required for obtaining the desired effect on the skin, such skin care compositions generally contain an emollient component to control or neutralize any detrimental effects of the functional ingredient on the skin and/or to retain or improve, the condition of the skin.

The emollient materials useful in the sponge products and processes of this invention are generally organic oils or unctuous (fatty, waxy, slippery, greasy) solids, synthetic or of animal/vegetable or mineral origin, well known in the art for improving conditioning, relaxing, softening and/or soothing the skin. They are generally water insoluble or water-dispersible but may be water soluble. Examples of suitable emollient substances include liquid and solid petrolatum, silicones, theobroms, almond, orris, olive, palm, coconut, cottonseed, corn and other vegetable oils, sulfonated oils, cholesterol, lanolin and derivatives such as polyoxyethylenated and polyoxypropylenated lanolin, spermaceti, natural and synthetic fatty esters and salts such as polyglycol stearate, glyceryl mono-, di- and tri-stearates, isopropyl sebacate and myristate, sorbitan sesquioleate and calcium and aluminum stearates, higher fatty alcohols such as cetyl, oleyl and stearyl alcohols, polyethylene glycol, e.g. M.W. 1500 and mixtures thereof and the like.

According to a preferred embodiment of the invention, there is included in the aqueous skin care compositions employed in the practice of this invention a surfactant, preferably those which are nonionically or anionically surface active. These surfactants, in addition to stabilizing and improving the foaming action and cell structure of the sponge, perform multiple functions in the said skin care compositions and the resulting impregnated sponge products of the invention. Thus, they act as emulsifying or dispersing agents for dispersing the composition in the water reactant medium and subsequently in the remoistening aqueous medium, facilitate the skin treating use of the sponge product, improve the uniformity of the resulting film of skin care composition on the skin, and perform a simultaneous detersive function on the skin.

Suitable surfactants of the nonionic type include, for example, polyoxyethylenated higher molecular weight reactive hydrogen-containing compounds such as the reaction products of about 2 to 30 moles of ethylene oxide with 1 mole of such compounds containing about 6 to 20 or more carbon atoms including fatty acids such as palmitic acid, monohydric and polyhydric alcohols such as Oxotridecyl alcohol (from tetrapropylene or triisobutylene), oleylalcohol, lauryl alcohol and polyoxypropylene glycol, and alkyl phenols such as nonyl phenol, and mixtures thereof and the like.

Suitable surfactants of the anionic type include the sodium, potassium, ammonium and amine salts of the sulfate and primary and secondary phosphate esters of the above-described polyoxyethylenated nonionic surfactants, such salts of fatty acids (soaps), of alkyl aryl sulfonic acids such as dodecylbenzene sulfonic acid, of fatty alcohol sulfates and phosphates such as lauryl sulfate and phosphate, of the sarcosinic acids, of lauryl sulfoacetic acid, of N-acyl taurides such as N-oleoyl-N-methyl tauride, of higher ethers and esters of isethionic acid, and mixtures thereof and the like.

In preparing the sponge products of this invention, there are in general employed, by weight of the prepolymer, about 30 to 200% and preferably about 60 to 120% of tap or deionized water, about 6 to 100% and preferably about 10 to 30% of the skin care composition of which about 5 to 100% may be an emollient substance, and preferably about 2 to 12% of the surfactant, the higher ranges of about 6 to 12% of the surfactant being preferred when a simultaneous cleansing function on the skin is desired.

Other known types of surfactants may be included in the aqueous reactant to stabilize and improve the cell or pore structure of the sponge, such as from about 0.5 to 5%, by weight of the prepolymer, of Union Carbide's Silicone L-520, Dow Corning DC-200 silicone stabilizer, and the like.

In some instance, some degree of simultaneous abrading action on the skin may be desired, for example to remove dead tissue or the like. For this purpose a small amount, for example, about 0.5 to 5%, of a finely divided abrasive material having a maximum diameter less than the pore size of the sponge structure may be included to permit the material to be readily released from the sponge. Generally, such abrasive particles should have a diameter ranging from about 1 to 100 microns. Examples of suitable abrasive materials include without limitation kaolin, clay, diatomaceous earth, calcium carbonate, pumice, talc, chromium oxide, iron oxide, fused synthetic aluminum oxide, garnet, permetite, feldspar, and the like. Such materials may be admixed with either the aqueous reactant or the non-aqueous prepolymer reactant.

Another useful additive to the water reactant, generally in weight concentrations of about 0.02 to 2%, is an emulsion stabilizer, thickener and/or protective colloid such as triethanolamine sulfate, carboxymethylcellulose, polyvinylpyrrolidone, polyacrylic acid, and the water insoluble but water swellable acidic carboxylic cross-linked polymers commercially available as Carbopols and disclosed in U.S. Pat. Nos. 2,798,053; 2,923,692 and 2,980,655.

Other optional additives to the water reactant include dyes, stains, pigments, UV absorbers (0.2–0.5%), optical brighteners (0.02–5%), antistatic agents (0.03–1%), wet slip improvers such as Union Carbide's Polyox water soluble resin, perfumes, germicides such as hexachlorophene, polyvinyl pyrrolidone-iodine complex iodophor, and phenoxypolyethoxyethanol-iodine iodophor, sequestering agents such as tetrasodium ethylenediamine tetraacetic acid, and the like. Insoluble additives in particulate form may be admixed with the water reactant or the prepolymer.

The foaming or sponge-producing reaction between the described aqueous skin care composition (water reactant) and the isocyanate-capped prepolymer is carried out in known manner, as by simply and quickly thoroughly mixing them prior to initiation of substantial gas bubble formation, pouring the mixture into a mold, on a moving belt or the like, or employing injection procedures, and permitting the foam to rise and set. The reaction is exothermic, and may be controlled if desired within a temperature range of about 10° to 100° C. Higher temperatures within this range hasten the reaction, as would inclusion of known catalysts such as tin compounds, for example stannous octoate, and amines, for example trimethyl amine, N-methyl- and N-ethyl-morpholine and the like.

Following completion of the foaming reaction, generally in about 1 to 10 minutes, the impregnated sponge product is preferably dried, if desired under vacuum of about 1 to 760 Torr at a temperature of about 0° to 150° C. and may be cut to any desired size.

If desired, about 2 to 20%, preferably about 5 to 10%, of diisocyanate reactant, preferably tolylene diisocyanate, or other cross-linking agent, by weight of the prepolymer may be preliminarily admixed therewith for the purpose of obtaining a lower density, larger pore size sponge structure. Adjustment of the above proportions and/or other known means may be employed to produce a more flexible or more rigid foam or sponge structure. Increased hardness and/or rigidity may for example be particularly desirable if a simultaneous abrading action on the skin is needed.

The following examples are only illustrative of preferred embodiments of this invention. All parts and proportions referred to herein and in the appended claims are by weight unless otherwise indicated.

PREPOLYMER A

A solution of 92 grams of glycerol representing 1 mole, 3 eq. OH, and 1000 grams of polyoxyethylene glycol 1000 representing 1 mole, 2 eq. OH is outgassed at 100° C. and 10 Torr for 2 hours. To the outgassed solution is added 870 grams representing 5 moles tolylene diisocyanate consisting of an 80/20 mixture of 2,4/2,6 isomers. The reaction solution is stirred at 60° C. for 4 hours whereupon the actual isocyanate content reaches a constant 2.49 meq. NCO/gram relative to a theoretical content of 2.54. The resin product has a pale orange color, a density of 1.10 and a viscosity (Brookfield No. 4 spindle) at 25° C. of 13,400 cps. 31.3 parts of the resin product representing 50 mole percent has a theoretical molecular weight of 615 as represented by the reaction product of 1 mole of glycerol with 3 moles of tolylene diisocyanate, while 68.7 parts of the resin product representing 50 mole percent has a theoretical molecular weight of 1348 as represented by the reaction product of 1 mole of polyoxyethylene glycol, M.W. 1000, with 2 moles of tolylene diisocyanate.

PREPOLYMER B

The above procedure is repeated except for using a polyoxyethylene glycol having a weight average molecular weight of 4,000. Corresponding results are obtained.

PREPOLYMER C

A slurry of 100 grams of pentaerythritol, 0.735 mole having 2.94 eq. OH in 860 grams of tolylene diisocyanate, 4.95 moles having 9.9 eq. NCO groups/gram and the mixture ratio of 80/20 of 2,4/2,6 isomers is stirred for 24 hours. An orange solution results. To the orange solution is added 1000 grams outgassed polyoxyethylene glycol representing 1 mole having 2.0 eq. OH. These reactants are stirred at about 67° C. for 4 hours followed by additional stirring at 25° C. for 16 hours whereupon the isocyanate content reaches a constant level of 2.63 meq. NCO groups/gram relative to a theoretical value of 2.56. The resultant product has an orange color, a viscous consistency at 25° C., and upon analysis is found to be a solution of about 31 percent by weight (42.5 mole percent) of the reaction product of 1 mole of pentaerythritol with 4 moles of tolylene diisocyanate having a theoretical molecular weight of 832, in about 69 percent by weight (57.5 mole percent) of the reaction product of 1 mole of polyethylene glycol, M.W. 1000 with 2 moles of tolylene diisocyanate having a theoretical molecular weight of 1348.

EXAMPLE 1

| PART I | 0.4 gram | Herbal Floral perfume |
| --- | --- | --- |
|  | 40.0 grams | floating bath oil consisting of 1% Solulan PB-20 emollient liquid (1 mole lanolin alcohol reacted with 20 moles propylene oxide-Amerchol) 5% Ameroxol OE-2 water-in-oil emulsifier liquid (1 mole oleyl alcohol reacted with 2 moles ethylene oxide, fragranted-Amerchol). 10% Acetulan spreading, penetrating, degreasing and emollient liquid agent (acetylated lanolin alcohol-Amerchol) 56% mineral oil (70 vis.) 28% isopropyl palmitate |
| PART II | 14.0 grams | Pluronic L-64* |
|  | 86.0 grams | tap water |
| PART III | 200.00 grams | PREPOLYMER A |

*Reaction product of 60% polyoxypropylene glycol M.W. 1750 with 40% ethylene oxide-Wyandotte.

Part I is thoroughly dispersed in Part II, and the resulting mixture added all at once to Part III, (previously fluidized by warming to 50° C.) with vigorous agitation which is continued until creaming occurs (about 30 seconds) caused by initial formation of visible $CO_2$ bubbles. The mixture is then poured into a 9"×9"×2" Teflon-coated pan and the foam allowed to rise and set or cure (within about 5–7 minutes). The resulting impregnated hydrophilic flexible open-celled poly (urea/urethane) sponge product, desirably after drying at room or elevated temperatures up to 100° C., and cutting to any desired size, is found to be highly effective as a skin conditioner and cleanser during a number of bathings until depleted of the impregnated skin care composition.

EXAMPLE 2

The procedure of Example 1 is repeated using PREPOLYMER B as Part III. Similar results are obtained.

EXAMPLE 3

The procedure of Example 1 is repeated using PREPOLYMER C as Part III. Similar results are obtained.

EXAMPLE 4

The procedure of Example 1 is repeated except that the floating bath oil is replaced by 4.0 grams of the same said mineral oil, the resulting sponge product being highly effective as a skin conditioner, softener and make-up remover during many use cycles till depleted of the skin care composition.

EXAMPLES 5 and 6

The procedure of Example 4 is repeated using, respectively, PREPOLYMERS B and C as Part III. Similar results are obtained.

EXAMPLE 7

The procedure of Example 1 is repeated except that the floating bath oil is replaced by 35.0 grams of Solution PB-2, a soft solid reaction product of 1 mole of lanolin alcohol with 2 moles of propyleneoxide (Amerchol). The resulting sponge product is similar to that of Example 4.

EXAMPLES 8 and 9

The procedure of Example 7 is repeated using, respectively, PREPOLYMERS B AND C as Part III. Similar results are obtained.

This invention has been disclosed with respect to certain preferred embodiments, and it will be understood that various modifications and variations thereof which will become obvious to persons skilled in the art are included within the spirit and purview of this application and the scope of the appended claims.

What is claimed is:

1. A method of preparing hydrophilic open-celled poly (urea/urethane) sponge comprising reacting (a) a prepolymer having an average NCO functionality greater than 2 and produced by reaction of a polyoxyethylene polyol with a stoichiometric excess of an organic polyisocyanate, with (b) about 30 to 200% of water by weight of said prepolymer, said water containing about 6 to 100%, by weight of said prepolymer, of a readily releasable skin care composition, said sponge thereby containing said skin care composition substantially uniformly distributed throughout the pores thereof.

2. A method as defined in claim 1 wherein said organic polyisocyanate is tolylene diisocyanate.

3. A method as defined in claim 1 wherein said organic polyisocyanate is an 80:20 isomeric mixture of 2,4- and 2,6-tolylene diisocyanate.

4. A method as defined in claim 1 wherein said composition contains at least one member of the group consisting of emollient oils, emollient solids and surface active agents.

5. A method as defined in claim 1 wherein said composition contains a surface active agent.

6. A method as defined in claim 5 wherein said surface active agent is nonionic.

7. A method as defined in claim 5 wherein said surface active agent is polyoxyethylenated polyoxypropylene glycol.

8. A method as defined in claim 5 wherein said composition also contains an emollient mineral oil.

9. A method as defined in claim 5 wherein said composition also contains a solid emollient lanolin compound.

10. A method as defined in claim 9 wherein said composition also contains an emollient mineral oil.

* * * * *